United States Patent
Iwahama et al.

(10) Patent No.: US 7,985,866 B2
(45) Date of Patent: Jul. 26, 2011

(54) VINYL ETHER COMPOUNDS AND POLYMERIZABLE COMPOSITIONS

(75) Inventors: Takahiro Iwahama, Himeji (JP); Tatsuya Nakano, Himeji (JP); Keizo Inoue, Himeji (JP); Hiroto Miyake, Himeji (JP); Tsukasa Yoshida, Himeji (JP); Mitsuru Ohno, Himeji (JP); Yoshinori Funaki, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 618 days.

(21) Appl. No.: 12/076,625

(22) Filed: Mar. 20, 2008

(65) Prior Publication Data

US 2008/0234455 A1 Sep. 25, 2008

(30) Foreign Application Priority Data

Mar. 23, 2007 (JP) .................. 2007-076219
Mar. 26, 2007 (JP) .................. 2007-078858

(51) Int. Cl.
*C07D 305/14* (2006.01)
*C07D 305/00* (2006.01)
(52) U.S. Cl. .................. 549/332; 549/511
(58) Field of Classification Search .......... 549/332, 549/511
See application file for complete search history.

(56) References Cited

U.S. PATENT DOCUMENTS

| 3,417,102 | A | 12/1968 | Braun et al. |
| 3,673,216 | A | 6/1972 | Schroeter |
| 5,166,265 | A | 11/1992 | Nakahata et al. |
| 5,605,941 | A | 2/1997 | Steinmann et al. |

FOREIGN PATENT DOCUMENTS

| EP | 0646580 A2 | 4/1995 |
| EP | 1095938 A1 | 5/2001 |
| GB | 1101789 A | 1/1968 |
| JP | 7-233112 A | 9/1995 |
| JP | 10-25262 A | 1/1998 |
| JP | 10-316670 A | 12/1998 |
| JP | 11-171967 A | 6/1999 |
| JP | 2003-73321 A | 3/2003 |
| JP | 2005-221716 A | 8/2005 |
| JP | 2007-76049 A | 3/2007 |

OTHER PUBLICATIONS

Hirabayashi, K., "Presensitized lithographic plates with good printability and storage stability, photosensitive compositions therefore, and laser platemaking thereof", Database CA [Online], Chemical Abstract Service, Columbus, Ohio, XP-002526242.
Hosokawa, T. et al., "Ink-jet printer heads in ink-jet printers", Database CA [Online], Chemical Abstract Service, Columbus, Ohio, XP-002526243.
Crivello, J.V. and S. Liu, "Free Radical Induced Acceleration of Cationic Photopolymerization", Chem. Mater, vol. 10, 1998, pp. 3724-3731. XP-002526241.
Machine Translation of JP 10-316670.
Machine Translation of JP 11-171967.

*Primary Examiner* — Janet L. Andres
*Assistant Examiner* — Raymond Covington
(74) *Attorney, Agent, or Firm* — Birch, Stewart, Kolasch & Birch, LLP

(57) ABSTRACT

Disclosed is an oxetane-containing vinyl ether compound including one or more aromatic or non-aromatic carbocycles and/or two or more vinyl ether structures, such as a compound of Formula:

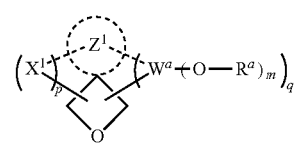

(1)

wherein Ring $Z^1$ is non-aromatic carbocycle; $R^a$ is vinyl group of Formula:

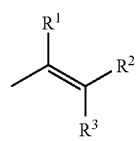

(2)

wherein each of $R^1$, $R^2$, and $R^3$ is hydrogen or C1-C4 alkyl; $W^a$ is single bond or organic group having a valence of (m+1); $X^1$ is, for example, hydrocarbon; "m" and "q" are each 1 or 2; and "p" is 0 to 5. Also disclosed is an alicyclic epoxy-containing vinyl ether compound of Formula:

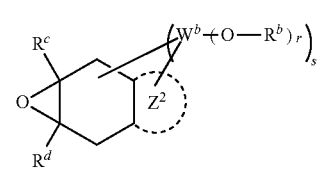

(3)

wherein Ring $Z^2$ is non-aromatic carbocycle; $R^b$ is vinyl group of Formula:

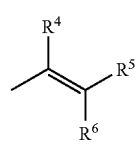

(4)

wherein $R^4$, $R^5$ and $R^6$ are each hydrogen or C1-C4 alkyl; $W^b$ is single bond or organic group having a valence of (r+1); $R^c$ and $R^d$ are hydrogen or alkyl; and "r" and "s" are 1 or 2.

4 Claims, No Drawings

VINYL ETHER COMPOUNDS AND POLYMERIZABLE COMPOSITIONS

BACKGROUND OF THE INVENTION

1. Field of the Invention

The present invention relates to oxetane-containing vinyl ether compounds and alicyclic epoxy-containing vinyl ether compounds (these are hereinafter also synthetically referred to as vinyl ether compounds). It also relates to polymerizable compositions containing the vinyl ether compounds and cured articles derived from the polymerizable compositions. These vinyl ether compounds are useful as polymerizable compounds that will polymerize or cure by the application of light and/or heat and are usable in the fields typically of materials for pharmaceutical chemicals, agricultural chemicals, coating agents, inks, paints and varnishes, adhesives, resists, plate-making materials, optical waveguides, holograms, and nanoimprint compositions.

2. Description of the Related Art

Polymerizable compounds that will polymerize or cure by the application of light and/or heat are widely utilized as materials for polymers typically in coating agents, inks, paints and varnishes, adhesives, resists, and plate-making materials. Epoxy compounds have been used as the polymerizable compounds. Known epoxy compounds are disadvantageous in handleability and safety, since they have low reactivity in polymerization (curability) and show high skin irritation and high toxicity, although they give cured articles that excel in chemical resistance and adhesion.

On the other hand, Japanese Unexamined Patent Application Publication (JP-A) No. Hei 10-25262 and JP-A No. 2003-73321 disclose some alicyclic vinyl ether compounds as polymerizable compounds. These compounds, however, are still susceptible to improvements, since they do not sufficiently rapidly cure or they give cured articles having insufficient hardness when used as materials for coatings or inks, although they have low skin irritation and are improved in workability (handleability). JP-A No. Hei 10-316670 discloses a vinyl ether compound having an oxetane ring in the molecule. This compound, however, does not sufficiently rapidly cure, and it gives cured articles that are still insufficient in transparency and thermal stability.

JP-A No. Hei 07-233112 and JP-A No. Hei. 11-171967 disclose vinyl ether compounds each intramolecularly containing an alicyclic epoxy group composed of a cyclohexane ring attached to an oxirane ring. Even these compounds, however, do not sufficiently rapidly cure, and they give cured articles that are still insufficient in transparency and thermal stability.

SUMMARY OF THE INVENTION

Under such circumstances, it is desirable to provide a novel oxetane-containing vinyl ether compound or a novel alicyclic epoxy-containing vinyl ether compound; a polymerizable composition containing the vinyl ether compound; and a cured article derived from the polymerizable composition.

It is also desirable to provide an oxetane-containing vinyl ether compound or an alicyclic epoxy-containing vinyl ether compound which rapidly cures and gives a cured article that excels in transparency and thermal stability; a polymerizable composition containing the vinyl ether compound; and a cured article derived from the polymerizable composition.

After intensive investigations, the present inventors have found that a specific vinyl ether compound containing an oxetane ring sufficiently rapidly cures and gives a cured article that excels in transparency and thermal stability. This oxetane-containing vinyl ether compound contains at least one carbocyclic ring and/or two or more vinyl ether structures per molecule.

In addition, the present inventors also have found that a specific vinyl ether compound containing an alicyclic epoxy group (1,2-epoxycyclohexyl group) sufficiently rapidly cures and gives a cured article that excels in transparency and thermal stability. This alicyclic epoxy-containing vinyl ether compound contains a non-aromatic carbocyclic ring in a specific position in the molecule and/or contains an alkyl group at a junction site between a cyclohexane ring constituting the alicyclic epoxy group and an oxirane ring. The present invention has been made based on these findings.

Specifically, according to an embodiment of the present invention, there is provided an oxetane-containing vinyl ether compound which contains (a) at least one oxetane ring; and (b) one or more aromatic or non-aromatic carbocyclic rings and/or two or more vinyl ether structures per molecule.

This oxetane-containing vinyl ether compound includes an oxetane-containing vinyl ether compound represented by following Formula (1):

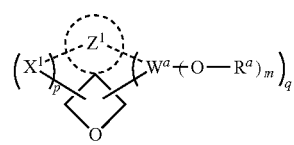

(1)

wherein Ring $Z^1$ may be present or absent in molecule and, if present, represents a non-aromatic carbocyclic ring that forms a spiro structure with oxetane ring; $R^a$ represents a substituted or unsubstituted vinyl group represented by following Formula (2):

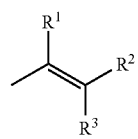

(2)

wherein each of $R^1$, $R^2$, and $R^3$ independently represents hydrogen atom or an alkyl group containing one to four carbon atoms; $W^a$ is a linkage connecting between a substituted or unsubstituted vinyloxy group (—$OR^a$ group) and oxetane ring or Ring $Z^1$ and represents a single bond or an organic group having a valence in the number of (m+1); $X^1$ is a substituent of oxetane ring and Ring $Z^1$ and represents a halogen atom, a substituted or unsubstituted hydrocarbon group, a protected or unprotected hydroxyl group, a protected or unprotected amino group, a protected or unprotected carboxyl group, a protected or unprotected sulfo group, oxo group, nitro group, cyano group, or a protected or unprotected acyl group; "m" denotes 1 or 2; "p" denotes an integer of from 0 to 5; and "q" denotes 1 or 2, in which when any of "m", "p", and "q" is 2 (or more), corresponding two (or more) parenthesized substituents may be the same as or different from each other, and, when "m" and "q" are both 1, at least one of following conditions (1), (2), and (3) is satisfied: (1) Ring $Z^1$ is present, (2) $X^1$ contains one or more aromatic or non-aromatic carbocyclic rings, and (3) $W^a$ contains one or more aromatic or non-aromatic carbocyclic rings.

According to another embodiment of the present invention, there is provided an alicyclic epoxy-containing vinyl ether compound which is represented by following Formula (3):

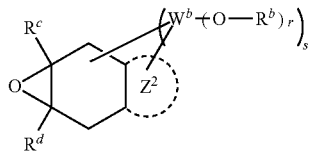
(3)

wherein Ring $Z^2$ may be present or absent in molecule and, if present, represents a non-aromatic carbocyclic ring; $R^b$ represents a substituted or unsubstituted vinyl group represented by following Formula (4):

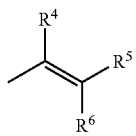
(4)

wherein each of $R^4$, $R^5$ and $R^6$ independently represents hydrogen atom or an alkyl group containing one to four carbon atoms; $W^b$ is a linkage connecting between a substituted or unsubstituted vinyloxy group (—$OR^b$ group) and cyclohexane ring or Ring $Z^2$ and represents a single bond or an organic group having a valence in the number of (r+1); each of $R^c$ and $R^d$ independently represents hydrogen atom or an alkyl group; "r" denotes 1 or 2; and "s" denotes 1 or 2, in which, when any of "r" and "s" is 2, corresponding two parenthesized substituents may be the same as or different from each other, and, provided that when $R^c$ and $R^d$ are both hydrogen atoms, satisfy at least one of following (i), (ii), and (iii); (i) Ring $Z^2$ is present, (ii) $W^b$ is a group represented by following Formula (5),

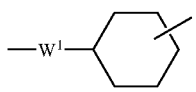
(5)

wherein $W^1$ represents a single bond or a bivalent organic group, and wherein a carbon atom constituting cyclohexane ring is attached to —$OR^b$ group, (iii) "s" is 2 and "r" is 1 and $W^b$ does not contain carbonyl group.

According to still another embodiment of the present invention, there is provided a polymerizable composition which contains (i) the oxetane-containing vinyl ether compound and/or the alicyclic epoxy-containing vinyl ether compound, and (ii) a polymerization initiator.

According to yet another embodiment of the present invention, there is provided a cured article as a polymerized product derived from the polymerizable composition.

As used herein "vinyl ether compound" and "vinyl ester compound" also include compounds in which hydrogen atom of whose vinyl group is substituted by a substituent.

These oxetane-containing vinyl ether compounds and alicyclic epoxy-containing vinyl ether compounds according to embodiments of the present invention, when used as material monomers for polymers, sufficiently rapidly cure upon application of heat and/or light and give cured articles that excel in transparency and thermal stability. In addition, they show low toxicity and low skin irritation. They are therefore advantageously used in the fields typically of materials for coating agents, inks, paints and varnishes, adhesives, resists, plate-making materials, optical waveguides, holograms, and nanoimprint compositions.

DESCRIPTION OF THE PREFERRED EMBODIMENTS

Oxetane-containing vinyl ether compounds according to an embodiment of the present invention are vinyl ether compounds which contain, in addition to an oxetane ring, one or more aromatic or non-aromatic carbocyclic rings and/or two or more vinyl ether structures per molecule. The vinyl ether compounds having this configuration are highly advantageous in that they sufficiently rapidly cure and give cured articles that excel in properties such as transparency and thermal stability.

Examples of the aromatic carbocyclic ring include benzene ring and naphthalene ring. Examples of the non-aromatic carbocyclic ring include cycloalkane rings such as cyclopropane ring, cyclobutane ring, cyclopentane ring, cyclohexane ring, cyclooctane ring, and cyclododecane ring, of which cycloalkane rings containing three to fifteen members are preferred; and bridged alicyclic rings containing six to twenty carbon atoms, such as decahydronaphthalene ring, adamantane ring, and norbornane ring. The vinyl ether compounds may have two or more aromatic or non-aromatic carbocyclic rings per molecule. The aromatic or non-aromatic carbocyclic ring(s) may often exist at a linkage site connecting between a vinyl ether structure and oxetane ring. A non-aromatic carbocyclic ring, if present, may form a spiro structure with the oxetane ring.

The oxetane-containing vinyl ether compounds may have one vinyl ether structure per molecule when they contain one or more aromatic or non-aromatic carbocyclic rings. They may contain no aromatic or non-aromatic carbocyclic ring when they have two or more vinyl ether structures. However, they may contain both one or more aromatic or non-aromatic carbocyclic rings and two or more vinyl ether structures per molecule.

In an embodiment, the oxetane-containing vinyl ether compounds include a compound of Formula (1). In Formula (1), Ring $Z^1$ represents a non-aromatic carbocyclic ring that forms a spiro structure with oxetane ring. Ring $Z^1$ may be present or absent in the molecule. Examples of the non-aromatic carbocyclic ring in Ring $Z^1$ are as with the above-listed non-aromatic carbocyclic rings. $Z^1$ is preferably cyclopentane ring or cyclohexane ring.

In Formula (1), $R^a$ is a substituted or unsubstituted vinyl group of Formula (2). In Formula (2), each of $R^1$, $R^2$, and $R^3$ is independently hydrogen atom or an alkyl group containing one to four carbon atoms. Examples of the alkyl group containing one to four carbon atoms include linear alkyl groups containing one to four carbon atoms, such as methyl, ethyl, propyl, and butyl, of which those containing one to three carbon atoms are preferred; branched alkyl groups containing one to four carbon atoms, such as isopropyl, isobutyl, s-butyl, and t-butyl, of which those containing one to three carbon atoms are preferred. Each of $R^1$, $R^2$, and $R^3$ is independently preferably hydrogen atom or methyl group. Representative examples of the group of Formula (2) include vinyl group, isopropenyl group, 1-propenyl group, 2-methyl-1-propenyl group, and 1,2-dimethyl-1-propenyl group.

In Formula (1), $W^a$ is a linkage connecting between a substituted or unsubstituted vinyloxy group (—$OR^a$ group) and oxetane ring or Ring $Z^1$ and represents a single bond or an organic group having a valence in the number of (m+1). The organic group may generally be a group that includes a carbon atom at a bonding site with an adjacent oxygen atom. Preferred examples as the organic group include (i) hydrocarbon groups, and (ii) groups each containing one or more hydrocarbon groups and at least one selected from oxygen atom (—O—), sulfur atom (—S—), carbonyl group (—CO—), and amino group (—NH—).

The hydrocarbon groups include aliphatic hydrocarbon groups, alicyclic hydrocarbon groups, aromatic hydrocarbon groups, and hydrocarbon groups as an assembly of two or more of these groups.

Taking bivalent hydrocarbon groups as an example, such hydrocarbon groups include linear or branched alkylene groups containing one to twenty carbon atoms, such as methylene, methylmethylene (ethylidene), ethylmethylene (propylidene), dimethylmethylene (isopropylidene), ethylmethylmethylene, ethylene, propylene, trimethylene, tetramethylene, and hexamethylene groups, of which those containing one to ten carbon atoms are preferred, and those containing one to six carbon atoms are more preferred; linear or branched alkenylene groups containing two to twenty carbon atoms, such as propenylene group, of which those containing two to ten carbon atoms are preferred, and those containing two to six carbon atoms are more preferred; cycloalkylene groups containing three to twenty members, such as 1,3-cyclopentylene, 1,2-cyclohexylene, 1,3-cyclohexylene, and 1,4-cyclohexylene groups, of which those containing three to fifteen members are preferred, and those containing five to eight members are more preferred; cycloalkylidene groups containing three to twenty members, such as cyclopropylidene, cyclopentylidene, and cyclohexylidene groups, of which those containing three to fifteen members are preferred, and those containing five to eight members are more preferred; arylene groups such as 1,2-phenylene, 1,3-phenylene, and 1,4-phenylene groups; and benzylidene group.

The hydrocarbon groups may each have one or more substituents. Examples of the substituents include protected or unprotected hydroxyl groups, protected or unprotected hydroxymethyl groups, protected or unprotected amino groups, protected or unprotected carboxyl groups, protected or unprotected sulfo groups, halogen atoms, oxo group, cyano group, nitro group, heterocyclic groups, hydrocarbon groups, and haloalkyl groups. Common protecting groups for use in organic synthesis can be utilized herein.

Examples of the heterocyclic groups as the substituents include heterocyclic groups that contain at least one hetero atom selected from nitrogen atom, oxygen atom, and sulfur atom and include three to fifteen members, of which heterocyclic groups containing five to eight members are preferred.

The hydrocarbon groups as the substituents include aliphatic hydrocarbon groups, alicyclic hydrocarbon groups, aromatic hydrocarbon groups, and groups as an assembly of two or more of these groups. Examples of the aliphatic hydrocarbon groups include alkyl groups containing one to twenty carbon atoms, of which those containing one to ten carbon atoms are preferred, and those containing one to three carbon atoms are more preferred; alkenyl groups containing two to twenty carbon atoms, of which those containing two to ten carbon atoms are preferred, and those containing two or three carbon atoms are more preferred; and alkynyl groups containing two to twenty carbon atoms, of which those containing two to ten carbon atoms are preferred, and those containing two or three carbon atoms are more preferred. Examples of the alicyclic hydrocarbon groups include cycloalkyl groups containing three to twenty members, of which those containing three to fifteen members are preferred, and those containing five to eight members are more preferred; cycloalkenyl groups containing three to twenty members, of which those containing three to fifteen members are preferred, and those containing five to eight members are more preferred; and bridged hydrocarbon groups such as perhydronaphth-1-yl group, norbornyl, adamantyl, and tetracyclo[4.4.0.1$^{2,5}$.1$^{7,10}$]dodec-3-yl groups. Examples of the aromatic hydrocarbon groups include aromatic hydrocarbon groups containing six to fourteen carbon atoms, of which those containing six to ten carbon atoms are preferred. Examples of hydrocarbon groups as an assembly of an aliphatic hydrocarbon group and an alicyclic hydrocarbon group include cycloalkyl-alkyl groups such as cyclopentylmethyl, cyclohexylmethyl, and 2-cyclohexylethyl groups, of which preferred are cycloalkyl-alkyl groups whose cycloalkyl moiety contains three to twenty carbon atoms and whose alkyl moiety contains one to four carbon atoms. Examples of hydrocarbon groups as an assembly of an aliphatic hydrocarbon group and an aromatic hydrocarbon group include aralkyl groups such as aralkyl groups containing seven to eighteen carbon atoms; and alkyl-substituted aryl groups such as phenyl group or naphthyl group on which one to four alkyl groups containing about one to about four carbon atoms are substituted.

Examples of the haloalkyl groups as the substituents include haloalkyl groups containing one to ten carbon atoms, such as chloromethyl, trifluoromethyl, 2,2,2-trifluoroethyl, and pentafluoroethyl groups, of which haloalkyl groups containing one to three carbon atoms are preferred.

Preferred examples of $W^a$ include a group represented by following Formula (6):

(6)

wherein $A^1$ is a bivalent hydrocarbon group; $Y^1$ is an oxygen atom (—O—), sulfur atom (—S—), carbonyl group (—CO—), amino group (—NH—), or a group as an assembly of two or more of these; $A^2$ is a single bond or a hydrocarbon group having a valence in the number of (m+1) where $A^2$ is attached to —$OR^a$; each of "t" and "u" is independently 0 or 1; and "v" is an integer of 0 to 5.

Examples of the bivalent hydrocarbon group as $A^1$ are as mentioned above. Among them, preferred as $A^1$ are linear or branched alkylene groups containing one to six carbon atoms, such as methylene, ethylene, propylene, isopropylidene, trimethylene, and tetramethylene groups.

Preferred examples as $Y^1$ include oxygen atom (—O—), sulfur atom (—S—), carbonyl group (—CO—), amino group (—NH—), —COO—, —OCO—, —CONH—, and —NHCO—.

Examples of the hydrocarbon group having a valence in the number of (m+1) as $A^2$ are as mentioned above. Among them, $A^2$ is preferably a single bond; or one of linear or branched alkylene groups containing one to six carbon atoms, such as methylene, ethylene, propylene, isopropylidene, trimethylene, and tetramethylene groups, cycloalkylene groups containing five to eight members, such as 1,3-cyclopentylene, 1,2-cyclohexylene, 1,3-cyclohexylene, and 1,4-cyclohexylene groups, cycloalkylidene groups containing five to eight members, such as cyclopropylidene, cyclopentylidene, and cyclohexylidene groups, and arylene groups such as 1,2-phenylene, 1,3-phenylene, and 1,4-phenylene groups, and groups as an assembly of two or more of these groups.

$W^a$ is particularly preferably a single bond; a linear or branched alkylene group containing one to six carbon atoms; or a group as an assembly of the alkylene group with oxygen atom or sulfur atom.

In Formula (1), $X^1$ is a substituent of oxetane ring and Ring $Z^1$ and represents a halogen atom, a substituted or unsubstituted hydrocarbon group, a protected or unprotected hydroxyl group, a protected or unprotected amino group, a protected or unprotected carboxyl group, a protected or unprotected sulfo group, an oxo group, a nitro group, a cyano group, or a protected or unprotected acyl group. Examples of the protecting groups herein include common protecting groups for use in organic synthesis.

Examples of the halogen atom as $X^1$ include fluorine, chlorine, and bromine atoms. Examples of the hydrocarbon group of the "substituted or unsubstituted hydrocarbon group" as $X^1$ include aliphatic hydrocarbon groups such as methyl, ethyl, propyl, isopropyl, butyl, isobutyl, s-butyl, t-butyl, hexyl, octyl, and decyl groups, of which alkyl groups containing one to ten carbon atoms are preferred, and alkyl groups containing one to five carbon atoms are more preferred; alicyclic hydrocarbon groups such as cyclopentyl and cyclohexyl groups, of which cycloalkyl groups containing three to fifteen members are preferred; aromatic hydrocarbon groups such as phenyl and naphthyl groups; and groups as an assembly of two or more of these groups. Examples of substituents which may be possessed by these hydrocarbon groups include halogen atoms such as fluorine, chlorine, and bromine atoms; alkyl groups containing one to four carbon atoms, such as methyl group; haloalkyl groups containing about one to about five carbon atoms, such as trifluoromethyl group; hydroxyl group; alkoxy groups containing one to four carbon atoms, such as methoxy group; amino group; dialkylamino group; carboxyl group; alkoxycarbonyl groups such as methoxycarbonyl group; nitro group; cyano group; and acyl groups such as acetyl group.

Examples of the acyl group as $X^1$ include aliphatic acyl groups containing one to six carbon atoms, such as formyl, acetyl, propionyl, butyryl, isobutyryl, and pivaloyl groups; acetoacetyl group; and aromatic acyl group such as benzoyl group.

When there are two or more $X^1$s, they may be combined to form a ring with a carbon atom constituting Ring $Z^1$ or oxetane ring in Formula (1). Examples of such ring include alicyclic carbocyclic rings such as cyclopentane ring, cyclohexane ring, and perhydronaphthalene ring (decahydronaphthalene ring); and lactone rings such as γ-butyrolactone ring and δ-valerolactone ring.

In Formula (1), "m" denotes 1 or 2 and is preferably 1; "p" denotes an integer of from 0 to 5 and is preferably an integer of from 0 to 3; and "q" denotes 1 or 2. When any of "m", "p", and "q" is 2 (or more), corresponding two (or more) parenthesized substituents may be the same as or different from each other. When "m" and "q" are both 1, at least one of following conditions (1), (2), and (3) is satisfied: (1) Ring $Z^1$ is present, (2) $X^1$ contains one or more aromatic or non-aromatic carbocyclic rings, and (3) $W^a$ contains one or more aromatic or non-aromatic carbocyclic rings.

Of compounds of Formula (1), preferred are compounds respectively represented by following Formulae (1a), (1b), (1c), and (1d):

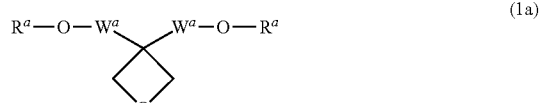

(1a)

(1b)

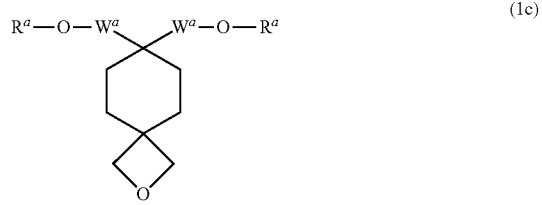

(1c)

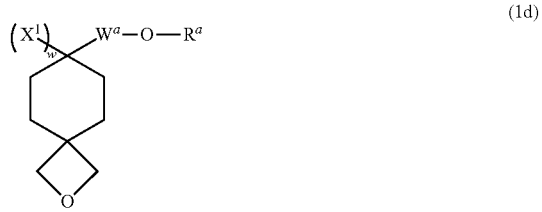

(1d)

wherein "w" is 0 or 1; and $R^a$, $W^a$, and $X^1$ are as defined above, where at least one of $W^a$ and $X^1$ in Formula (1b) contains one or more aromatic or non-aromatic carbocyclic rings.

Representative examples of oxetane-containing vinyl ether compounds according to embodiments of the present invention include the following compounds. In these formulae (I-1), (I-2), "n" is an integer of from 0 to 6.

(1-1)

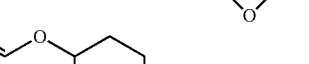

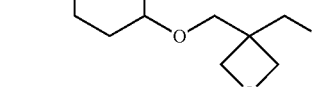

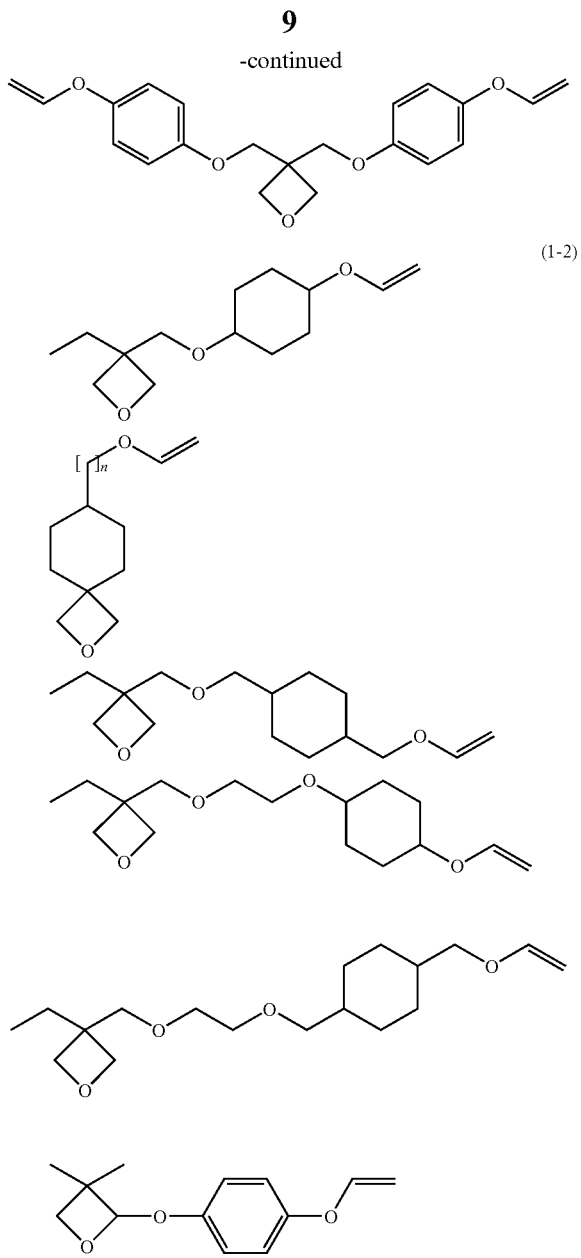

Oxetane-containing vinyl ether compounds according to embodiment of the present invention can be prepared utilizing one or more reactions known as processes for the preparation of vinyl ether compounds. In a preferred embodiment, oxetane-containing vinyl ether compounds are prepared by a process of reacting alcohols (hydroxy compounds) with vinyl ester compounds, each corresponding to the oxetane-containing vinyl ether compounds, in the presence of one or more transition element compounds. Typically, an oxetane-containing vinyl ether compound of Formula (1) can be prepared by reacting an alcohol (hydroxy compound) corresponding to Formula (1), except with $R^a$ being hydrogen atom, with a corresponding vinyl ester compound in the presence of a transition element compound.

Representative examples of the vinyl ester compound include a vinyl ester compound represented by following Formula (7):

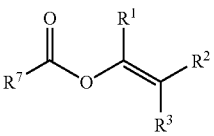

(7)

wherein each of $R^1$, $R^2$ and $R^3$ is independently hydrogen atom or an alkyl group containing one to four carbon atoms; and $R^7$ is hydrogen atom or an organic group.

In the vinyl ester compound of Formula (7), $R^1$, $R^2$, and $R^3$ are as described above. The organic group as $R^7$ can be any group that does not adversely affect the reaction, and examples thereof include the organic groups listed as the alkyl group containing one to four carbon atoms typically as $R^1$. Representative examples of the vinyl ester compound of Formula (7) include vinyl acetate, isopropenyl acetate, 1-propenyl acetate, 2-methyl-1-propenyl acetate, 1,2-dimethyl-1-propenyl acetate, vinyl formate, vinyl propionate, and vinyl benzoate.

A reaction can proceed under mild conditions according to the above-mentioned process, since one or more transition element compounds (including elementary transition elements) are used as a catalyst. Each of transition element compounds can be used alone or in combination. Examples of the transition elements include, of the Periodic Table of Elements, elements belonging to Group IIIA, typified by lanthanoid elements (lanthanum series elements); elements belonging to Group VA; elements belonging to Group VIA; elements belonging to Group VIIA; elements belonging to Group VIII, as iron, cobalt, nickel, ruthenium, rhodium, palladium, osmium, iridium, and platinum; and elements belonging to Group IB. Among them, elements belonging to Group VIII are preferred, of which platinum group elements (ruthenium, rhodium, palladium, osmium, iridium, and platinum) are more preferred, and iridium is particularly preferred.

Examples of transition element compounds include inorganic compounds such as elementary transition elements (metals), oxides, sulfides, hydroxides, halides (fluorides, chlorides, bromides, and iodides), sulfates, oxo acids containing one or more transition elements, and salts thereof, and inorganic complexes; and organic compounds including cyanides, salts of organic acids (e.g., acetates), and organic complexes. Among them, organic complexes are preferred. Ligands of the complexes include known ligands. The valence of transition elements in these transition element compounds is about 0 to about 6, and preferably 0 to 3. In the case typically of iridium compounds, the valence is preferably 1 or 3. Namely, iridium compounds for use herein preferably contain monovalent or trivalent iridium. Such transition element compounds can be used as intact or as being supported by carriers.

The amount of transition element compounds is, for example, about 0.0001 to about 1 mole, preferably about 0.001 to about 0.3 mole, and more preferably about 0.005 to about 0.1 mole, per 1 mole of the hydroxy compound used as a reaction component.

The reaction between the vinyl ester compound of Formula (7) and the hydroxy compound is performed in the presence of or in the absence of a solvent. Examples of the solvent include aliphatic hydrocarbons such as hexane, heptane, and octane; alicyclic hydrocarbons such as cyclohexane; aromatic hydrocarbons such as benzene, toluene, xylenes, and ethylbenzene; halogenated hydrocarbons such as chloroform, dichloromethane, and 1,2-dichloroethane; ethers such as diethyl ether, dimethoxyethane, tetrahydrofuran, and dioxane; ketones such as acetone and methyl ethyl ketone; esters such as methyl acetate, ethyl acetate, isopropyl acetate, and butyl acetate; amides such as N,N-dimethylformamide and N,N-dimethylacetamide; and nitriles such as acetonitrile, propionitrile, and benzonitrile. Each of these solvents can be used alone or in combination.

The amount of the vinyl ester compound of Formula (7) is, for example, about 0.8 to about 10 equivalents, preferably about 1 to about 8 equivalents, and more preferably about 1.5 to about 5 equivalents, to 1 equivalent of the hydroxy compound. The vinyl ester compound of Formula (7) may be used in large excess.

In general, the reaction can proceed more rapidly when the reaction system further contains a base. Such bases for use herein include inorganic bases and organic bases. Examples of the inorganic bases include hydroxides of alkali metals, such as lithium hydroxide, sodium hydroxide, potassium hydroxide, and cesium hydroxide; hydroxides of alkaline earth metals, such as magnesium hydroxide, calcium hydroxide, and barium hydroxide; carbonates of alkali metals, such as lithium carbonate, sodium carbonate, potassium carbonate, and cesium carbonate; carbonates of alkaline earth metals, such as magnesium carbonate; and hydrogen carbonates of alkali metals, such as lithium hydrogen carbonate, sodium hydrogen carbonate, potassium hydrogen carbonate, and cesium hydrogen carbonate.

Examples of the organic bases include organic acid salts of alkali metals, such as lithium acetate, sodium acetate, potassium acetate, and cesium acetate, of which alkali metal acetates are preferred; organic acid salts of alkaline earth metals, such as magnesium acetate; alkoxides of alkali metals, such as lithium methoxide, sodium methoxide, sodium ethoxide, sodium isopropoxide, and potassium ethoxide, of which alkoxides of alkali metals corresponding to the hydroxy compound are preferred; phenoxides of alkali metals such as sodium phenoxide; amines such as triethylamine and N-methylpiperidine, of which tertiary amines are preferred; and nitrogen-containing aromatic heterocyclic compounds such as pyridine, 2,2'-bipyridyl, and 1,10-phenanthroline. Among these bases, sodium-containing bases are preferred.

The amount of the base is, for example, about 0.001 to about 3 moles, and preferably about 0.005 to about 2 moles, per 1 mole of the hydroxy compound.

The reaction may be performed in the presence of a polymerization inhibitor. A reaction temperature can be set as appropriate according typically to types of reaction components and catalyst and is, for example, about 20° C. to about 200° C., preferably about 50° C. to about 150° C., and more preferably about 70° C. to about 120° C. The reaction may be performed under normal pressure, under reduced pressure, or under pressure (under a load). The reaction atmosphere is not particularly limited, as long as not adversely affecting the reaction, and can be any atmosphere such as air atmosphere, nitrogen atmosphere, or argon atmosphere. The reaction can be performed according to any system such as a batch system, semibatch system, or continuous system. The progression of the vinylation reaction can be controlled by adjusting a reaction time period. Typically, a dihydroxy compound containing two hydroxyl groups per molecule gives a monovinyl compound with one vinyloxy group introduced thereto and one hydroxyl group remained in a reaction for a short time period such as about two hours, and it gives a divinyl compound with two vinyloxy groups introduced thereto in a reaction for a longer time period such as about five hours.

The reaction yields a corresponding oxetane-containing vinyl ether compound of Formula (1) under mild conditions.

After the completion of reaction, reaction products can be separated and purified by a separation procedure such as filtration, concentration, distillation, extraction, crystallization, recrystallization, or column chromatography, or any combination of these separation procedures.

An alicyclic epoxy-containing vinyl ether compound according to another embodiment of the present invention is a compound of Formula (3). This compound is a vinyl ether compound that contains an alicyclic epoxy group (a group containing 1,2-epoxycyclohexane ring, i.e., 7-oxabicyclo[4.1.0]heptane ring) and further contains one or more non-aromatic carbocyclic ring at specific position in the molecule and/or contains an alkyl group at the junction site between cyclohexane ring constituting the alicyclic epoxy group and oxirane ring. Vinyl ether compounds of this type are much advantageous in that they sufficiently rapidly cure and give cured articles that excel in properties such as transparency and thermal stability.

In Formula (3), Ring $Z^2$ may be present or absent in the molecule, and, if present, represents a non-aromatic carbocyclic ring. Examples of the non-aromatic carbocyclic ring include cycloalkane rings such as cyclopropane ring, cyclobutane ring, cyclopentane ring, cyclohexane ring, cyclooctane ring, and cyclododecane ring, of which cycloalkane rings containing three to fifteen members are preferred; and bridged alicyclic rings containing six to twenty carbon atoms, such as decahydronaphthalene (perhydronaphthalene) ring and norbornane ring.

In Formula (3), $R^b$ is a substituted or unsubstituted vinyl group of Formula (4). In Formula (4), each of $R^4$, $R^5$ and $R^6$ is independently hydrogen atom or an alkyl group containing one to four carbon atoms. Examples of the alkyl group containing one to four carbon atoms include linear alkyl groups containing one to four carbon atoms, such as methyl, ethyl, propyl, and butyl, of which those containing one to three carbon atoms are preferred; and branched alkyl groups containing one to four carbon atoms, such as isopropyl, isobutyl, s-butyl, and t-butyl, of which those containing one to three carbon atoms are preferred. Each of $R^4$, $R^5$, and $R^6$ is independently preferably hydrogen atom or methyl group. Representative examples of the group of Formula (4) include vinyl group, isopropenyl group, 1-propenyl group, 2-methyl-1-propenyl group, and 1,2-dimethyl-1-propenyl group.

In Formula (3), $W^b$ is a linkage connecting between a substituted or unsubstituted vinyloxy group (—$OR^b$ group) and cyclohexane ring or Ring $Z^2$ and represents a single bond or an organic group having a valence in the number of (r+1). The organic group may generally be a group that includes a carbon atom at a bonding site with an adjacent oxygen atom. Preferred examples as the organic group include (i) hydrocarbon groups, and (ii) groups each containing one or more hydrocarbon groups and at least one selected from oxygen atom (—O—), sulfur atom (—S—), carbonyl group (—CO—), and amino group (—NH—).

The hydrocarbon groups (i) include aliphatic hydrocarbon groups, alicyclic hydrocarbon groups, aromatic hydrocarbon groups, and hydrocarbon groups as an assembly of two or more of these groups.

Taking bivalent hydrocarbon groups as an example, such hydrocarbon groups include linear or branched alkylene groups containing one to twenty carbon atoms, such as methylene, methylmethylene (ethylidene), ethylmethylene (propylidene), dimethylmethylene (isopropylidene), ethylmethylmethylene, ethylene, propylene, trimethylene, tetramethylene, and hexamethylene groups, of which those containing one to ten carbon atoms are preferred, and those containing one to six carbon atoms are more preferred; linear or branched alkenylene groups containing two to twenty carbon atoms, such as propenylene group, of which those containing two to ten carbon atoms are preferred, and those containing two to six carbon atoms are more preferred; cycloalkylene groups containing three to twenty members, such as 1,3-cyclopentylene, 1,2-cyclohexylene, 1,3-cyclohexylene, and 1,4-cyclohexylene groups, of which those containing three to fifteen members are preferred, and those containing five to eight members are more preferred; cycloalkylidene groups containing three to twenty members, such as cyclopropylidene, cyclopentylidene, and cyclohexylidene groups, of which those containing three to fifteen members are preferred, and those containing five to eight members are more preferred; arylene groups such as 1,2-phenylene, 1,3-phenylene, and 1,4-phenylene groups; and benzylidene group.

The hydrocarbon groups may each have one or more substituents. Examples of the substituents include protected or unprotected hydroxyl groups, protected or unprotected hydroxymethyl groups, protected or unprotected amino groups, protected or unprotected carboxyl groups, protected or unprotected sulfo groups, halogen atoms, oxo group, cyano group, nitro group, heterocyclic groups, hydrocarbon groups, and haloalkyl groups. Common protecting groups for use in organic synthesis can be utilized herein.

Examples of the heterocyclic groups as the substituents include heterocyclic groups that contain at least one hetero atom selected from nitrogen atom, oxygen atom, and sulfur atom and include three to fifteen members, of which heterocyclic groups containing five to eight members are preferred.

The hydrocarbon groups as the substituents include aliphatic hydrocarbon groups, alicyclic hydrocarbon groups, aromatic hydrocarbon groups, and groups as an assembly of two or more of these groups. Examples of the aliphatic hydrocarbon groups include alkyl groups containing one to twenty carbon atoms, of which those containing one to ten carbon atoms are preferred, and those containing one to three carbon atoms are more preferred; alkenyl groups, containing two to twenty carbon atoms, of which those containing two to ten carbon atoms are preferred, and those containing two or three carbon atoms are more preferred; and alkynyl groups containing two to twenty carbon atoms, of which those containing two to ten carbon atoms are preferred, and those containing two or three carbon atoms are more preferred. Examples of the alicyclic hydrocarbon groups include cycloalkyl groups containing three to twenty members, of which those containing three to fifteen members are preferred, and those containing five to eight members are more preferred; cycloalkenyl groups containing three to twenty members, of which those containing three to fifteen members are preferred, and those containing five to eight members are more preferred; and bridged hydrocarbon groups such as perhydronaphth-1-yl group, norbornyl, adamantyl, and tetracyclo[4.4.0.1$^{2,5}$.1$^{7,10}$]dodec-3-yl groups. Examples of the aromatic hydrocarbon groups include aromatic hydrocarbon groups containing six to fourteen carbon atoms, of which those containing six to ten carbon atoms are preferred. Examples of hydrocarbon groups as an assembly of an aliphatic hydrocarbon group and an alicyclic hydrocarbon group include cycloalkyl-alkyl groups such as cyclopentylmethyl, cyclohexylmethyl, and 2-cyclohexylethyl groups, of which preferred are cycloalkyl-alkyl groups whose cycloalkyl moiety contains three to twenty carbon atoms and whose alkyl moiety contains one to four carbon atoms. Examples of hydrocarbon groups as an assembly of an aliphatic hydrocarbon group and an aromatic hydrocarbon group include aralkyl groups such as aralkyl groups containing seven to eighteen carbon atoms; and alkyl-substituted aryl groups such as phenyl group or naphthyl group on which one to four alkyl groups containing one to four carbon atoms are substituted.

Examples of the haloalkyl groups as the substituents include haloalkyl groups containing one to ten carbon atoms, such as chloromethyl, trifluoromethyl, 2,2,2-trifluoroethyl, and pentafluoroethyl groups, of which those containing one to three carbon atoms are preferred.

Preferred examples of $W^b$ include a group represented by following Formula (8):

wherein $A^3$ is a bivalent hydrocarbon group; $Y^2$ is an oxygen atom (—O—), sulfur atom (—S—), carbonyl group (—CO—), amino group (—NH—), or an assembly of two or more of these groups; $A^4$ is a single bond or a hydrocarbon group having a valence in the number of (r+1), where $A^4$ is attached to —OR$^b$; each of "x" and "y" is independently 0 or 1; and "z" is an integer of from 0 to 5.

Examples of the bivalent hydrocarbon group as $A^3$ are as mentioned above. Among them, preferred as $A^3$ are linear or branched alkylene groups containing one to six carbon atoms, such as methylene, ethylene, propylene, isopropylidene, trimethylene, and tetramethylene groups.

Preferred examples as $Y^2$ include oxygen atom (—O—), sulfur atom (—S—), carbonyl group (—CO—), amino group (—NH—), —COO—, —OCO—, —CONH—, and —NHCO—.

Examples of the hydrocarbon group having a valence in the number of (r+1) as $A^4$ are as mentioned above. Among them, preferred examples as $A^4$ include single bond; or a group selected from linear or branched alkylene groups containing one to six carbon atoms, such as methylene, ethylene, propylene, isopropylidene, trimethylene, and tetramethylene groups, cycloalkylene groups containing five to eight members, such as 1,3-cyclopentylene, 1,2-cyclohexylene, 1,3-cyclohexylene, and 1,4-cyclohexylene groups, cycloalkylidene groups containing five to eight members, such as cyclopropylidene, cyclopentylidene, and cyclohexylidene groups, arylene groups such as 1,2-phenylene, 1,3-phenylene, and 1,4-phenylene groups, and groups as an assembly of two or more of these groups.

$W^b$ is particularly preferably a single bond; a linear or branched alkylene group containing one to t six carbon atoms; or a group as an assembly of the alkylene group with at least one group selected from oxygen atom (—O—), sulfur atom (—S—), and carbonyl group (—CO—).

The bonding position of the group $W^b$ in the cyclohexane ring or Ring $Z^2$ is not particularly limited. When Ring $Z^2$ is absent, $W^b$ is preferably bonded at the 4-position and/or the 5-position provided that the junction positions in cyclohexane ring with oxirane ring are defined as the 1-position and 2-position.

In Formula (3), each of $R^c$ and $R^d$ is independently hydrogen atom or an alkyl group. Examples of the alkyl group include linear or branched alkyl groups containing one to fifteen carbon atoms, such as methyl, ethyl, propyl, isopropyl, butyl, isobutyl, s-butyl, t-butyl, hexyl, octyl, and decyl groups. Among them, alkyl groups containing one to six carbon atoms are preferred, of which those containing one to three carbon atoms, such as methyl group, are more preferred.

In Formula (3), "r" denotes 1 or 2 and is preferably 1; and "s" denotes 1 or 2. When any of "r" and "s" is 2, corresponding two parenthesized substituents may be the same as or different from each other, and, provided that when $R^c$ and $R^d$ are both hydrogen atoms, satisfy at least one of following (i), (ii), and (iii); (i) Ring $Z^2$ is present, (ii) $W^b$ is a group represented by preceding Formula (5), (iii) "s" is 2 and "r" is 1, and $W^b$ does not contain carbonyl group.

In Formula (5), $W^1$ is a single bond or a bivalent organic group. Examples of the bivalent organic group include bivalent hydrocarbon groups, and groups as an assembly of a bivalent hydrocarbon group with at least one selected from oxygen atom (—O—), sulfur atom (—S—), carbonyl group (—CO—), and amino group (—NH—). The bivalent hydrocarbon groups are as described above. $W^1$ is particularly preferably a single bond or an alkyleneoxy group containing one to six carbon atoms whose oxygen atom is attached to the cyclohexane group in the right hand in Formula (5).

Of compounds of Formula (3), preferred are compounds respectively represented by following Formulae (3a), (3b), (3c) and (3d):

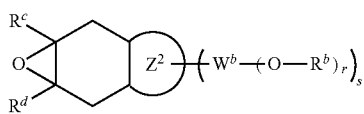
(3a)

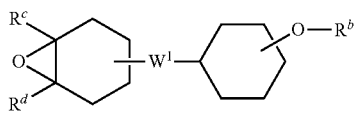
(3b)

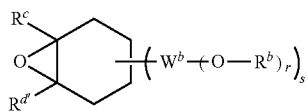
(3c)

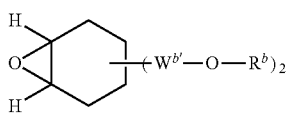
(3d)

wherein $R^{d'}$ is an alkyl group containing one to six carbon atoms; and Ring $Z^2$, $R^b$, $R^c$, $R^d$, $W^b$, $W^1$, "r", and "s" are as defined above, where $W^b$ in Formula (3a) connects between the —$OR^b$ group and Ring $Z^2$, in Formula (3d), $W^{b'}$ is a single bond; a bivalent hydrocarbon group containing one to six carbon atoms; or a bivalent organic group in which one or more hydrocarbon group containing one to six carbon atoms is connected with at least one selected from the group consisting of oxygen atom (—O—), sulfur atom (—S—), and amino group (—NH—).

In Formula (3a), each of $R^c$ and $R^d$ is independently preferably hydrogen atom or an alkyl group containing one to six carbon atoms, and is more preferably hydrogen atom or an alkyl group containing one to three carbon atoms typified by methyl group. In another preferred embodiment, at least one of $R^c$ and $R^d$ is hydrogen atom. Ring $Z^2$ is preferably a cycloalkane ring containing five to twelve members, such as cyclopentane ring, cyclohexane ring, or cyclooctane ring; or a bridged alicyclic ring containing eight to fifteen carbon atoms, such as decahydronaphthalene ring or norbornane ring. $W^b$ is particularly preferably a single bond; a hydrocarbon group containing one to fifteen carbon atoms; or a group as an assembly of one or more hydrocarbon groups containing one to fifteen carbon atoms with at least one selected from oxygen atom (—O—), sulfur atom (—S—), carbonyl group (—CO—), and amino group (—NH—).

In Formula (3b), each of $R^c$ and $R^d$ is preferably independently hydrogen atom or an alkyl group containing one to six carbon atoms and is more preferably hydrogen atom or an alkyl group containing one to three carbon atoms, such as methyl group. In another preferred embodiment, at least one of $R^c$ and $R^d$ is hydrogen atom. $W^1$ is particularly preferably a single bond or an alkyleneoxy group containing one to six carbon atoms, whose oxygen atom is attached to the cyclohexane ring in the right hand in Formula (3b).

In Formula (3c), $R^c$ is preferably hydrogen atom or an alkyl group containing one to six carbon atoms, more preferably hydrogen atom or an alkyl group containing one to three carbon atoms, and particularly preferably hydrogen atom. $R^d$ is preferably an alkyl group containing one to three carbon atoms, and more preferably methyl group. $W^b$ is preferably a single bond, a hydrocarbon group containing one to fifteen carbon atoms, or a group as an assembly of one or more hydrocarbon groups containing one to fifteen carbon atoms with at least one selected from oxygen atom (—O—), sulfur atom (—S—), carbonyl group (—CO—), and amino group (—NH—).

In Formula (3d), $W^{b'}$ is preferably a single bond; a bivalent hydrocarbon group containing one to six carbon atoms.

Representative examples of the alicyclic epoxy-containing vinyl ether compounds according to embodiments of the present invention include following compounds. In the following formulae, (3-1), (3-2), "1" is 0 or 1; and $A^5$ is a linear or branched alkylene group containing two to ten carbon atoms and is preferably a linear or branched alkylene group containing two to six carbon atoms.

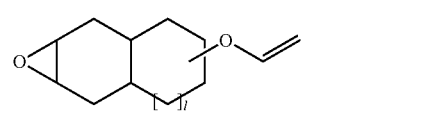
(3-1)

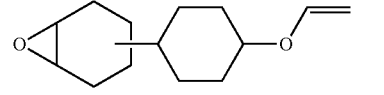

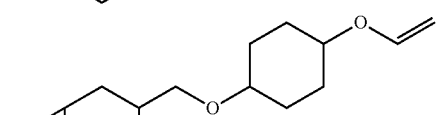

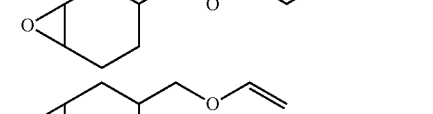

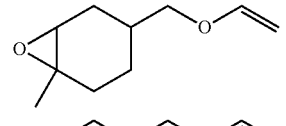
(3-2)

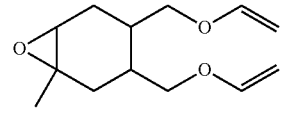

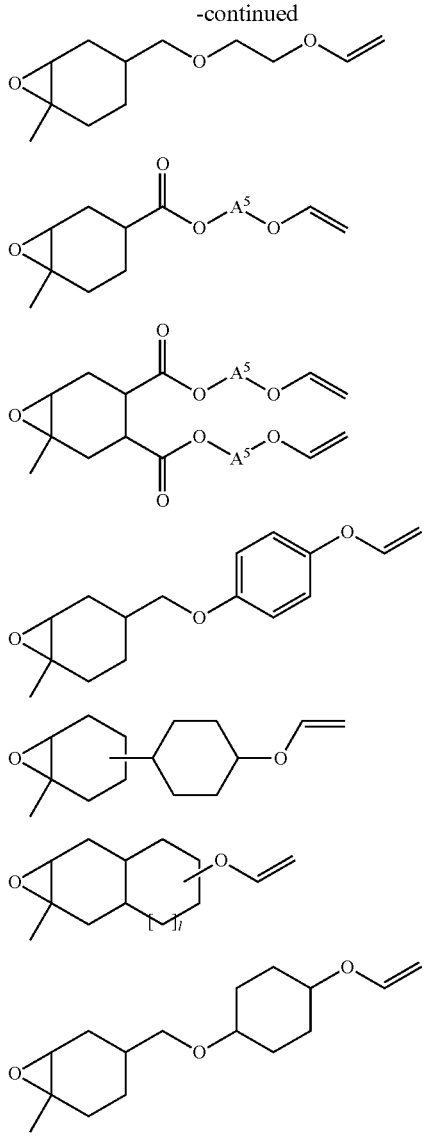

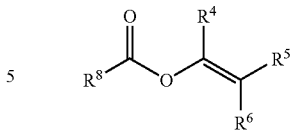

(9)

wherein each of $R^4$, $R^5$, and $R^6$ is independently hydrogen atom or an alkyl group containing one to four carbon atoms; and $R^8$ is hydrogen atom or an organic group.

In the vinyl ester compounds of Formula (9), $R^4$, $R^5$, and $R^6$ are as defined above. The organic group as $R^8$ can be any group that does not adversely affect the reaction, and examples thereof include the organic groups listed as the alkyl groups containing one to four carbon atoms typically as $R^4$. Representative examples of the vinyl ester compounds of Formula (9) include vinyl acetate, isopropenyl acetate, 1-propenyl acetate, 2-methyl-1-propenyl acetate, 1,2-dimethyl-1-propenyl acetate, vinyl formate, vinyl propionate, and vinyl benzoate.

A reaction can proceed under mild conditions according to the above-mentioned process, since one or more transition element compounds (including elementary transition elements) are used as a catalyst. Each of transition element compounds can be used alone or in combination. Examples of the transition elements include, of the Periodic Table of Elements, elements belonging to Group IIIA typified by lanthanoid elements (lanthanum series elements); elements belonging to Group VA; elements belonging to Group VIA; elements belonging to Group VIIA; elements belonging to Group VIII, such as iron, cobalt, nickel, ruthenium, rhodium, palladium, osmium, iridium, and platinum; and elements belonging to Group IB. Among them, elements belonging to Group VIII are preferred, of which platinum group elements (ruthenium, rhodium, palladium, osmium, iridium, and platinum) are more preferred, and iridium is particularly preferred.

Examples of transition element compounds include inorganic compounds such as elementary transition elements (metals), oxides, sulfides, hydroxides, halides (fluorides, chlorides, bromides, and iodides), sulfates, oxo acids containing one or more transition elements, and salts thereof, and inorganic complexes including cyanides, salts of organic acids (e.g., acetates), and organic complexes. Among them, organic complexes are preferred. Ligands of the complexes include known ligands. The valence of transition elements in these transition element compounds is about 0 to about 6, and preferably 0 to 3. In the case typically of iridium compounds, the valence is preferably 1 or 3. Namely, iridium compounds for use herein preferably contain monovalent or trivalent iridium. Such transition element compounds can be used as intact or as being supported by carriers.

The amount of transition element compounds is, for example, about 0.0001 to about 1 mole, preferably 0.001 to about 0.3 mole, and more preferably 0.005 to about 0.1 mole, per 1 mole of the hydroxy compound used as a reaction component.

The reaction between the vinyl ester compound of Formula (9) and the hydroxy compound is performed in the presence of or in the absence of a solvent. Examples of the solvent include aliphatic hydrocarbons such as hexane, heptane, and octane; alicyclic hydrocarbons such as cyclohexane; aromatic hydrocarbons such as benzene, toluene, xylenes, and ethylbenzene; halogenated hydrocarbons such as chloroform, dichloromethane, and 1,2-dichloroethane; ethers such as Alicyclic epoxy-containing vinyl ether compounds according to embodiments of the present invention can be prepared utilizing one or more reactions known as preparation processes for vinyl ether compounds. In a preferred embodiment, alicyclic epoxy-containing vinyl ether compounds are prepared by a process of reacting alcohols (hydroxy compounds) with vinyl ester compounds, each corresponding to the alicyclic epoxy-containing vinyl ether compounds, in the presence of one or more transition element compounds. Specifically, the alicyclic epoxy-containing vinyl ether compounds of Formula (3) can be prepared by reacting alcohols (hydroxy compounds) corresponding to Formula (3), except with $R^b$ being hydrogen atom, with corresponding vinyl ester compounds in the presence of one or more transition element compounds. Such alcohols (hydroxy compounds) corresponding to the alicyclic epoxy-containing vinyl ether compounds can be synthetically prepared from known compounds utilizing known reactions.

Representative examples of the vinyl ester compounds include a vinyl ester compound represented by following Formula (9):

diethyl ether, dimethoxyethane, tetrahydrofuran, and dioxane; ketones such as acetone and methyl ethyl ketone; esters such as methyl acetate, ethyl acetate, isopropyl acetate, and butyl acetate; amides such as N,N-dimethylformamide and N,N-dimethylacetamide; and nitrites such as acetonitrile, propionitrile, and benzonitrile. Each of these solvents can be used alone or in combination.

The amount of the vinyl ester compound of Formula (9) is, for example, about 0.8 to about 10 equivalents, preferably about 1 to about 8 equivalents, and more preferably about 1.5 to about 5 equivalents, to 1 equivalent of the hydroxy compound. The vinyl ester compound of Formula (9) may be used in large excess.

In general, the reaction can proceed more rapidly when the reaction system further includes a base. Such bases for use herein include inorganic bases and organic bases. Examples of the inorganic bases include hydroxides of alkali metals, such as lithium hydroxide, sodium hydroxide, potassium hydroxide, and cesium hydroxide; hydroxides of alkaline earth metals, such as magnesium hydroxide, calcium hydroxide, and barium hydroxide; carbonates of alkali metals, such as lithium carbonate, sodium carbonate, potassium carbonate, and cesium carbonate; carbonates of alkaline earth metals, such as magnesium carbonate; hydrogen carbonates of alkali metals, such as lithium hydrogen carbonate, sodium hydrogen carbonate, potassium hydrogen carbonate, and cesium hydrogen carbonate.

Examples of the organic bases include organic acid salts of alkali metals, such as lithium acetate, sodium acetate, potassium acetate, and cesium acetate, of which alkali metal acetates are preferred; organic acid salts of alkaline earth metals, such as magnesium acetate; alkoxides of alkali metals, such as lithium methoxide, sodium methoxide, sodium ethoxide, sodium isopropoxide, and potassium ethoxide, of which alkoxides of alkali metals corresponding to the oxygen-containing polycyclic hydroxy compound are preferred; phenoxides of alkali metals, such as sodium phenoxide; amines such as triethylamine and N-methylpiperidine, of which tertiary amines are preferred; and nitrogen-containing aromatic heterocyclic compounds such as pyridine, 2,2'-bipyridyl, and 1,10-phenanthroline. Among these bases, sodium-containing bases are preferred.

The amount of the base is, for example, about 0.001 to about 3 moles, and preferably about 0.005 to about 2 moles, per 1 mole of the hydroxy compound.

The reaction may be performed in the presence of a polymerization inhibitor. A reaction temperature can be set as appropriate according typically to types of reaction components and catalyst and is, for example, about 20° C. to about 200° C., preferably about 50° C. to about 150° C., and more preferably about 70° C. to about 120° C. The reaction may be performed under normal pressure, under reduced pressure, or under pressure (under a load). The reaction atmosphere is not particularly limited, as long as not adversely affecting the reaction, and can be any atmosphere such as air atmosphere, nitrogen atmosphere, or argon atmosphere. The reaction can be performed according to any system such as a batch system, semibatch system, or continuous system. The progression of the vinylation reaction can be controlled by adjusting a reaction time period. Typically, a dihydroxy compound containing two hydroxyl groups per molecule gives a monovinyl compound with one vinyloxy group introduced thereto and one hydroxyl group remained in a reaction for a short period of time typically of about two hours, and it gives a divinyl compound with two vinyloxy groups introduced thereto in a reaction for a longer period of time typically of about five hours.

The reaction yields a corresponding alicyclic epoxy-containing vinyl ether compound of Formula (3) under mild conditions. After the completion of reaction, reaction products can be separated and purified by a separation procedure such as filtration, concentration, distillation, extraction, crystallization, recrystallization, or column chromatography, or any combination of these separation procedures.

A polymerizable composition according to an embodiment of the present invention contains the oxetane-containing vinyl ether compound and/or alicyclic epoxy-containing vinyl ether compound each according to an embodiment of the present invention; and a polymerization initiator. The polymerization initiator can be any one that can induce or cause free-radical polymerization or ionic (cationic) polymerization, such as a thermal initiator, photo-induced free-radical polymerization initiator, or photo-induced cationic polymerization initiator. Typically, known polymerization initiators and light-activatable acid generators can be used herein. Examples of thermal initiators for use herein include benzoyl peroxide, acetyl peroxide, lauroyl peroxide, t-butyl hydroperoxide, azobisisobutyronitrile, azobis-(2,4-dimethylvaleronitrile), and azobis(cyclohexanecarbonitrile). Examples of photoinitiators include 2,4-diethylthioxanthone, benzophenone, 4-dimethylaminoisoamyl benzoate, and 4-dimethylaminoethyl benzoate; sulfonium salts such as triarylsulfonium hexafluorophosphates and triarylsulfonium hexafluoroantimonates, iodonium salts such as diaryliodonium hexafluorophosphates, diphenyliodonium hexafluoroantimonate, and bis(dodecylphenyl)iodonium tetrakis(pentafluorophenyl)borate, phosphonium salts such as tetrafluorophosphonium hexafluorophosphate, and pyridinium salts. Since the alicyclic epoxy-containing vinyl ether compound according to an embodiment of the present invention is likely to dissolve such a polymerization initiator therein, the polymerizable composition can be easily prepared.

The amount of the polymerization initiator is generally 0.01 to 50 percent by weight, and preferably 0.1 to 20 percent by weight, relative to the oxetane-containing vinyl ether compound or alicyclic epoxy-containing vinyl ether compound.

The polymerizable composition may further contain any of curable compounds other than the oxetane-containing vinyl ether compound and/or alicyclic epoxy-containing vinyl ether compound, as well as various additives, inorganic or organic particles, and fluorosilanes. Examples of the other curable compounds include epoxy compounds, oxetane compounds, and vinyl ether compounds. Examples of the additives include sensitizers such as anthracene based sensitizers. Examples of inorganic or organic particles include nanoscale particles. The content of the oxetane-containing vinyl ether compound and/or alicyclic epoxy-containing vinyl ether compound based on the total amount of curable compounds contained in the polymerizable composition is, for example, 20 percent by weight or more, preferably 50 percent by weight or more, and more preferably 70 percent by weight or more. The curable compounds in the polymerizable composition may be substantially composed of the oxetane-containing vinyl ether compound and/or alicyclic epoxy-containing vinyl ether compound according to an embodiment of the present invention alone.

The polymerizable composition according to an embodiment of the present invention sufficiently rapidly cure, since it contains the oxetane-containing vinyl ether compound and/or alicyclic epoxy-containing vinyl ether compound according to an embodiment of the present invention.

A cured article according to an embodiment of the present invention can be obtained by applying electron beams, radiation, or heat to the polymerization composition containing the oxetane-containing vinyl ether compound and/or alicyclic epoxy-containing vinyl ether compound according to an embodiment of the present invention. The resulting cured article is satisfactorily transparent and highly thermally stable. Accordingly, the oxetane-containing vinyl ether compounds and alicyclic epoxy-containing vinyl ether compounds according to embodiments of the present invention can be used, as polymerizable compounds that cure or polymerize by the application of light or heat, in the fields typically of materials for coating agents, inks, paints and varnishes, adhesives, resists, plate-making materials, optical waveguides, holograms, and nanoimprint compositions.

EXAMPLES

The present invention will be illustrated in further detail with reference to several examples below. It should be noted, however, these are illustrated only by way of example and never construed to limit the scope of the present invention.

Example 1

A mixture (280 mL) of 24.9 g (0.23 mol) of sodium carbonate and toluene was heated to a temperature of 95° C., and 1.4 g of propionic acid was added dropwise to the mixture. Next, maintaining the temperature of the reaction mixture, 16 g of vinyl acetate was added dropwise to the mixture, and fifteen minutes later, further the mixture was combined with 1.27 g (1.9 mmol) of di-μ-chlorobis(1,5-cyclooctadiene)diiridium(I) [Ir(cod)Cl]$_2$. Next, 40 g (0.19 mol) of oxetane-3,3-dimethanol was added dropwise for three hours, and a reaction was carried out in a nitrogen atmosphere while adding dropwise 79.8 g of vinyl acetate and maintaining the temperature of the reaction mixture. After the completion of dropwise addition, the mixture was stirred for one hour. As the result of gas chromatography analysis of the mixture, it is confirmed that there were produced 3,3-bis(vinyloxymethyl) oxetane represented by following Formula (10) in a yield of 90% and (3-vinyloxymethyloxetan-3-yl)methanol in a yield of 2%. Purification of the reaction mixture by distillation yielded 31 g of 3,3-bis(vinyloxymethyl)oxetane with a purity of 99%.

[Spectral Data of 3,3-Bis(vinyloxymethyl)oxetane]
$^1$H-NMR (CDCl$_3$) δ: 6.5 (2H, dd), 4.53 (4H, s), 4.2 (2H, d), 4.05 (2H, d), 3.93 (4H, s):

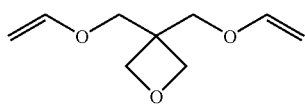

(10)

Example 2

To toluene (500 g) were added 3-chloromethyl-3-ethyloxetane (0.1 mol), 1,4-cyclohexanediol (0.5 mol), and tetrabutylammonium bromide (0.01 mol), the mixture was heated to 90° C., was combined with a 5 N aqueous sodium hydroxide solution (100 g) added dropwise, followed by stirring for five hours. The toluene solution (toluene layer) was washed with water, concentrated, purified by silica gel chromatography, and thereby yielded 4-(3-ethyloxetan-3-yl-methoxy)cyclohexanol with a purity of 99%.

A mixture (100 mL) of sodium carbonate (0.06 mol) and toluene was heated to 95° C. Maintaining the temperature of the reaction mixture, 4.2 g of vinyl acetate was added dropwise to the mixture, and fifteen minutes later, further the mixture was combined with di-μ-chlorobis(1,5-cyclooctadiene)diiridium(I) [Ir(cod)Cl]$_2$ (0.5 mmol). Next, 4-(3-ethyloxetan-3-yl-methoxy)cyclohexanol (0.05 mol) was added dropwise for two hours, and a reaction was then carried out in a nitrogen atmosphere while adding dropwise 12.6 g of vinyl acetate and holding the reaction temperature at 95° C. After the completion of dropwise addition, the mixture was stirred for one hour. As the result of gas chromatography analysis of the mixture, it is confirmed that there was produced 3-ethyl-3-(4-vinyloxycyclohexyloxymethyl) oxetane represented by following Formula (11) in a yield of 92%. In $^1$H-NMR (CDCl$_3$) analysis, signals specific to vinyl group were observed at 6.5 ppm, 4.2 ppm, and 4.04 ppm as in Example 1.

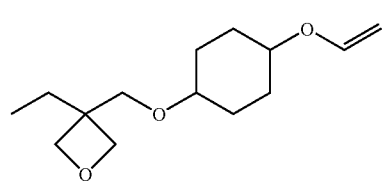

(11)

Example 3

4,5-di(hydroxymethyl)cyclohexene was epoxidized with m-chloroperbenzoic acid and thereby yielded 4,5-di(hydroxymethyl)cyclohexene oxide (cis-trans mixture). A mixture (280 mL) of sodium carbonate 24.9 g (0.23 mol) and toluene was heated to 95° C., and 1.4 g of propionic acid was added to the mixture. Maintaining the temperature of the reaction mixture, the mixture was combined with 19 g of vinyl acetate added dropwise, and fifteen minutes later, further combined with 1.27 g (1.9 mmol) of di-μ-chlorobis(1,5-cyclooctadiene)diiridium(I) [Ir(cod)Cl]$_2$. Next, 30 g (0.19 mol) of 4,5-di(hydroxymethyl)cyclohexene oxide (cis-trans mixture) was added dropwise for three hours, and a reaction was carried out in a nitrogen atmosphere while adding dropwise 62 g of vinyl acetate and holding the reaction temperature at 95° C. After the completion of dropwise addition, the mixture was stirred for one hour. As the result of gas chromatography analysis of the mixture, it is confirmed that there were produced 4,5-di(vinyloxymethyl)cyclohexene oxide (cis-trans mixture) represented by following Formula (12) in a yield of 82% and 4-vinyloxymethyl-5-hydroxymethyl cyclohexene oxide (cis-trans mixture) in a yield of 4%. Purification of the reaction mixture by distillation yielded 31 g of 4,5-di-(vinyloxymethyl)cyclohexene oxide (cis-trans mixture) with a purity of 98%.

[Spectral Data of 4,5-di(vinyloxymethyl)cyclohexene Oxide]
$^1$H-NMR (CDCl$_3$) δ cis-trans mixture: 6.46-6.26 (4H, m), 4.32-4.14 (4H, m), 4.18-4.14 (2H, m), 4.03-3.98 (6H, m), 3.91-3.90 (2H, m), 3.73-3.70 (2H, m), 3.49-3.47 (4H, m), 2.45-2.13 (2H, m), 2.23-1.79 (2H, m), 1.78-1.44 (2H, m):
Cis form was attributed to the following signals.
6.46-6.42 (2H, dd, J=6.7 and 7.9)
2.45-2.43 (2H, m)
2.23-2.20 (2H, dd, J=6.1 and 6.7)
1.78-1.75 (2H, m)

Trans form was attributed to the following signals.
6.30-6.26 (2H, dd, J=6.7 and 7.3)
2.15-2.13 (2H, m)
1.83-1.79 (2H, dd, J=6.1 and 6.7)
1.50-1.44 (2H, m)
1.50-1.44 (2H, m):

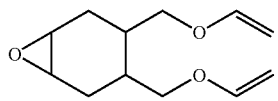

(12)

Example 4

4,5-di(hydroxymethyl)-1-methylcyclohexene was epoxidized with m-chloroperbenzoic acid and thereby yielded 4,5-di(hydroxymethyl)-1-methylcyclohexene oxide. A mixture (280 mL) of sodium carbonate 24.9 g (0.23 mol) and toluene was heated to 95° C., and 1.4 g of propionic acid was added dropwise to the mixture. Maintaining the temperature of the reaction mixture, the mixture was combined with 19 g of vinyl acetate added dropwise, and fifteen minutes later, further combined with 1.27 g (1.9 mmol) of di-μ-chlorobis(1,5-cyclooctadiene)diiridium(I) [Ir (cod) Cl]$_2$. Next, 30 g (0.19 mol) of 4,5-di(hydroxymethyl)-1-methylcyclohexene oxide was added dropwise for three hours, and a reaction was carried out in a nitrogen atmosphere while adding dropwise 62 g of vinyl acetate and holding the reaction temperature at 95° C. After the completion of dropwise addition, the mixture was stirred for one hour. As the result of gas chromatography analysis of the mixture, it is confirmed that there were produced 4,5-di(vinyloxymethyl)-1-methylcyclohexene oxide represented by following Formula (13) in a yield of 80%. In $^1$H-NMR (CDCl$_3$) analysis, signals specific to vinyl group were observed at 6.2-6.5 ppm, 4.1-4.3 ppm, as an isomer mixture.

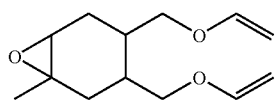

(13)

Examples 5 to 9 and Comparative Examples 1 to 4

In these examples and comparative examples, a curable composition (polymerizable composition) was prepared by admixing and dissolving (A) a vinyl ether compound, (B) a cyclic ether compound, and (C) a cationic light-activatable acid generator in amounts listed in Table 1.

A shape corresponding to a sample was cut out of a Teflon (registered trademark) plate with a thickness of 1 mm or 200 μm, both sides of the Teflon plate were sandwiched between a Teflon (registered trademark)-coated poly(ethylene terephthalate) (PET) film and a glass plate respectively in this order, to yield a laminate (glass plate/PET/Teflon (registered trademark)/PET/glass plate). The above-prepared curable composition was injected into the cut-out portion to be the sample shape with an injector, and then irradiated with ultraviolet rays (UV) using a conveyor-system ultraviolet irradiator under after-mentioned conditions. Thus, cured articles with a thickness of 1 mm and 200 μm, respectively, corresponding to the Teflon (registered trademark) plate used were obtained.

According to methods mentioned later, determinations were made on solubility of the cationic light-activatable acid generator (C) in the vinyl ether compound (A) or in a mixture of the vinyl ether compound (A) and the cyclic ether compound (B); curing rate of the prepared curable composition; and gel fraction, transmittance, and thermal stability of the prepared cured articles. The results are shown in Table 1.

Example 10

Epoxidation of 12.6 g (0.1 mol) of (4-methylcyclohex-3-enyl)methanol was carried out with a 5 percent by weight solution of peracetic acid in ethyl acetate at 65° C. Purification of the product by distillation yielded 12 g of (6-methyl-7-oxabicyclo[4.1.0]hept-3-yl)methanol with a purity of 98%.

A mixture (100 mL) of sodium carbonate (0.06 mol) and toluene was heated to 95° C. 4.2 g of vinyl acetate was added dropwise to the mixture. Next, maintaining the temperature of the reaction mixture, and fifteen minutes later, further the mixture was combined with di-μ-chlorobis(1,5-cyclooctadiene)diiridium(I) [Ir(cod)Cl]$_2$ (0.5 mmol). Next, (6-methyl-7-oxabicyclo[4.1.0]hept-3-yl)methanol (0.05 mol) was added dropwise over for two hours, and a reaction was carried out in a nitrogen atmosphere while adding dropwise 12.6 g of vinyl acetate and holding the reaction temperature at 95° C. After the completion of dropwise addition, the mixture was stirred for one hour. As the result of gas chromatography analysis of the mixture, it is confirmed that there was produced 1-methyl-4-vinyloxy-7-oxabicyclo[4.1.0]heptane represented by following Formula (14) in a yield of 95%. In $^1$H-NMR (CDCl$_3$) analysis, signals specific to vinyl group were observed at 6.5 ppm, 4.2 ppm, and 4.05 ppm.

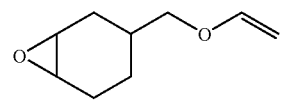

(14)

Example 11

To toluene (500 g) were added 4-chloromethylcyclohexene (0.1 mol), 1,4-cyclohexanediol (0.5 mol), and tetrabutylammonium bromide (0.01 mol), and the mixture was heated to 90° C. and combined with a 5 N aqueous sodium hydroxide solution (100 g) added dropwise, followed by stirring for a for hours. The toluene solution (toluene layer) was washed with water, concentrated, purified by silica gel chromatography, and thereby yielded 13 g of 4-(cyclohex-3-enylmethoxy)cyclohexanol with a purity of 99%.

Epoxidation was conducted by the procedure of Example 1, except for using above-prepared 4-(cyclohex-3-enylmethoxy)cyclohexanol instead of (4-methylcyclohex-3-enyl)methanol, and thereby yielded 8 g of 4-(7-oxabicyclo[4.1.0]hept-3-ylmethoxy)cyclohexanol.

In addition, vinyl-etherification was conducted by the procedure of Example 1, except for using above-prepared 4-(7-oxabicyclo[4.1.0]hept-3-ylmethoxy)cyclohexanol instead of (6-methyl-7-oxabicyclo[4.1.0]hept-3-yl)methanol, and thereby yielded 3-(4-vinyloxycyclohexyloxymethyl)-7-oxabicyclo[4.1.0]heptane represented by following Formula (15). In $^1$H-NMR (CDCl$_3$) analysis, signals specific to vinyl group were observed at 6.5 ppm, 4.2 ppm, and 4.04 ppm.

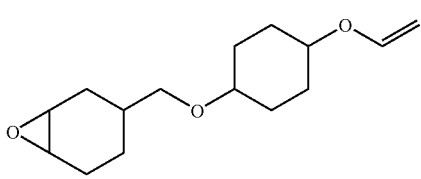

(15)

Examples 12 to 14 and Comparative Examples 5 to 8

In these examples and comparative examples, a curable composition (polymerizable composition) was prepared by admixing and dissolving (D) a vinyl ether compound, (B) a cyclic ether compound, and (C) a cationic light-activatable acid generator in amounts listed in Table 2.

A shape corresponding to a sample was cut out of a Teflon (registered trademark) plate with a thickness of 1 mm or 200 μm, both sides of the Teflon plate were sandwiched between a Teflon (registered trademark)-coated poly(ethylene terephthalate) (PET) film and a glass plate respectively in this order, to yield a laminate (glass plate/PET/Teflon (registered trademark)/PET/glass plate). The above-prepared curable composition was injected into the cut-out portion to be the sample shape with an injector, and then irradiated with ultraviolet rays (UV) with a conveyor-system ultraviolet irradiator under after-mentioned conditions. Thus, cured articles with a thickness of 1 mm and 200 μm, respectively, corresponding to the Teflon (registered trademark) plate used were obtained.

According to methods mentioned later, determinations were made on solubility of the cationic light-activatable acid generator (C) in the vinyl ether compound (D) or in a mixture of the vinyl ether compound (D) and the cyclic ether compound (B); curing rate of the prepared curable composition; and gel fraction, transmittance, and thermal stability of the prepared cured articles.

Conditions for Curing by Ultraviolet Rays:

UV irradiator: Ultraviolet irradiator "UVC-02516S1-AA02" supplied by Ushio Inc., with a metal halide lamp Irradiation power: 160 W Conveyor speed: 2 meters per minutes Irradiation time: Once The symbols in the vinyl ether compound (A), cyclic ether compound (B), and cationic light-activatable acid generator (C) in Table 1 are as follows:

Vinyl Ether Compound (A)

(A1): 3,3-Bis(vinyloxymethyl)oxetane prepared in Example 1

(A2): 3-Ethyl-3-(4-vinyloxycyclohexyloxymethyl)oxetane prepared in Example 2

(A3): 1,4-Cyclohexanedimethanol divinyl ether (supplied by Aldrich)

(A4): Tetraethylene glycol divinyl ether (supplied by Aldrich)

Cyclic Ether Compound (B)

(B1): "Celloxide 2021P" supplied by Daicel Chemical Industries, Ltd.

(B2): "ARON OXETANE OXT-121" supplied by Toagosei Co., Ltd.

Cationic Light-Activatable Acid Generator (C)

(C1): "Irgacure 250" supplied by Ciba Specialty Chemicals Corporation (C2): "PI 2074" supplied by Rhodia The symbols in the vinyl ether compound (D), cyclic ether compound (B), and cationic light-activatable acid generator (C) in Table 2 are as follows:

Vinyl Ether Compound (D)

(D1): 1-Methyl-4-vinyloxy-7-oxabicyclo[4.1.0]heptane prepared in Example 10

(D2): 3-(4-Vinyloxycyclohexyloxymethyl)-7-oxabicyclo[4.1.0]heptane prepared in Example 11

(D3): 1,4-Cyclohexanedimethanol divinyl ether (supplied by Aldrich)

(D4): Tetraethylene glycol divinyl ether (supplied by Aldrich)

Cyclic Ether Compound (B)

(B1): "Celloxide 2021P" supplied by Daicel Chemical Industries, Ltd.

(B2): "ARON OXETANE OXT-121" supplied by Toagosei Co., Ltd.

Cationic Light-Activatable Acid Generator (C)

(C1): "Irgacure 250" supplied by Ciba Specialty Chemicals Corporation (C2): "PI2074" supplied by Rhodia Evaluation Tests Solubility of Light-Activatable Acid Generator The cationic light-activatable acid generator (C) was added in an amount shown in Table 1 or 2 to the vinyl ether compound (A) or (D), or to a mixture of the vinyl ether compound (A) or (D) with the cyclic ether compound (B) to yield a composition, the composition was stirred for a period of fifteen minutes, visually observed, and the solubility of light-activatable acid generator was rated according to the following criteria:

Good: The cationic light-activatable acid generator (C) fully dissolved to yield a transparent curable composition.

Poor: The resulting composition was opaque or included precipitates of the cationic light-activatable acid generator (C).

Curing Rate

The curable composition was cured using the conveyor-system ultraviolet irradiator, and whether or not a cured article is obtained was observed.

Good: A cured article was obtained.

Poor: The composition was thickened and was not solidified (cured).

Gel Fraction

Each of the cured articles with a thickness of 200 μm prepared according to Examples and Comparative Examples was placed in methyl ethyl ketone (MEK) as a solvent for extraction, the initial weight before extraction and the weight after extraction and drying were measured, and the gel fraction was determined by calculation according to the following equation:

Gel fraction(%)=(Weight after extraction and drying)/(Initial weight before extraction)×100

Transmittance

Transmittance (%) at wavelengths of 400 nm, 550 nm, 700 nm, and 850 nm was measured on each of the cured articles with a thickness of 1 mm prepared in Examples and Comparative Examples. The measurement was done immediately after curing (initial) and after a heat treatment of the cured articles at 120° C. for one hour (after heating), using the Spectrophotometer "U-3300" (supplied by Hitachi Ltd.). The results are shown in "Initial transmittance" and "Transmittance after heating" in Tables 1 and 2.

Thermal Stability

The sample used in the measurement of transmittance was further placed in an oven at 200° C. for two hours, the loss in weight of the sample after this heat treatment was measured, and the thermal stability of the sample was rated according to the following criteria:

Good: Loss in weight was 5% or less.

Fair: Loss in weight was more than 5% and equal to or less than 10%.

Poor: Loss in weight was more than 10%.

TABLE 1

| | Ex. 5 | Ex. 6 | Ex. 7 | Ex. 8 | Ex. 9 | Com. Ex. 1 | Com. Ex. 2 | Com. Ex. 3 | Com. Ex. 4 |
|---|---|---|---|---|---|---|---|---|---|
| Composition (parts by weight) | | | | | | | | | |
| Vinyl ether compound (A) | | | | | | | | | |
| (A1) | 100 | 100 | 80 | 80 | | | | | |
| (A2) | | | | | 100 | | | | |
| (A3) | | | | | | 100 | 100 | 50 | |
| (A4) | | | | | | | | | 100 |
| Cyclic ether compound (B) | | | | | | | | | |
| (B1) | | | 20 | | | | | 50 | |
| (B2) | | | | 20 | | | | | |
| Cationic light-activatable acid generator (C) | | | | | | | | | |
| (C1) | 5 | | 5 | 5 | 5 | 5 | | 5 | 5 |
| (C2) | | 5 | | | | | 5 | | |
| Results | | | | | | | | | |
| Solubility of light-activatable acid generator | Good | Good | Good | Good | Good | Poor | Good | Good | Good |
| Curing rate | Good | Good | Good | Good | Good | — | Good | Good | Good |
| Gel fraction (%) | 95 | 94 | 95 | 94 | 95 | — | 92 | 93 | 90 |
| Initial transmittance (%) 400 nm | 89 | 88 | 89 | 88 | 88 | — | 10 | 88 | 12 |
| 550 nm | 90 | 90 | 90 | 90 | 90 | — | 45 | 90 | 45 |
| 700 nm | 90 | 90 | 90 | 90 | 90 | — | 87 | 90 | 83 |
| 850 nm | 90 | 90 | 90 | 90 | 90 | — | 87 | 90 | 86 |
| Transmittance after heating (%) 400 nm | 87 | 86 | 88 | 86 | 86 | — | 1 | 86 | 1 |
| 550 nm | 90 | 90 | 90 | 90 | 90 | — | 40 | 90 | 65 |
| 700 nm | 90 | 90 | 90 | 90 | 90 | — | 87 | 90 | 70 |
| 850 nm | 90 | 90 | 90 | 90 | 90 | — | 88 | 90 | 73 |
| Thermal stability | Good | Good | Good | Good | Good | — | Fair | Fair | Poor |

TABLE 2

| | Ex. 12 | Ex. 13 | Ex. 14 | Com. Ex. 5 | Com. Ex. 6 | Com. Ex. 7 | Com. Ex. 8 |
|---|---|---|---|---|---|---|---|
| Composition (parts by weight) | | | | | | | |
| Vinyl ether compound (D) | | | | | | | |
| (D1) | 100 | | | | | | |
| (D2) | | 100 | 80 | | | | |
| (D3) | | | | 100 | 100 | 50 | |
| (D4) | | | | | | | 100 |
| Cyclic ether compound (B) | | | | | | | |
| (B1) | | | 20 | | | 50 | |
| (B2) | | | | | | | |
| Cationic light-activatable acid generator (C) | | | | | | | |
| (C1) | 5 | 5 | 5 | 5 | | 5 | 5 |
| (C2) | | | | | 5 | | |
| Results | | | | | | | |
| Solubility of light-activatable acid generator | Good | Good | Good | Poor | Good | Good | Good |
| Curing rate | Good | Good | Good | — | Good | Good | Good |
| Gel fraction (%) | 93 | 92 | 94 | — | 92 | 93 | 90 |
| Initial transmittance (%) 400 nm | 88 | 88 | 90 | — | 10 | 88 | 12 |
| 550 nm | 90 | 90 | 91 | — | 45 | 90 | 45 |
| 700 nm | 90 | 90 | 91 | — | 87 | 90 | 83 |
| 850 nm | 90 | 90 | 91 | — | 87 | 90 | 86 |
| Transmittance after heating (%) 400 nm | 86 | 86 | 87 | — | 1 | 86 | 1 |
| 550 nm | 90 | 90 | 90 | — | 40 | 90 | 65 |
| 700 nm | 90 | 90 | 91 | — | 87 | 90 | 70 |
| 850 nm | 90 | 90 | 91 | — | 88 | 90 | 73 |
| Thermal stability | Good | Good | Good | — | Fair | Fair | Poor |

As is described above, according to embodiments of the present invention, there are provided oxetane-containing vinyl ether compounds and alicyclic epoxy-containing vinyl ether compounds that sufficiently rapidly cure and yield cured articles that excel in transparency and thermal stability.

While there has been described what is at present considered to be preferred embodiments of the present invention, it should be understood by those skilled in the art that various modifications, combinations, subcombinations, and alterations may occur depending on design requirements and other factors insofar as they are within the scope of the appended claims or the equivalents thereof.

What is claimed is:

1. An oxetane-containing vinyl ether compound comprising:
   (a) at least one oxetane ring; and
   (b) one or more aromatic or non-aromatic carbocyclic rings,
   two or more vinyl ether structures, or
   one or more aromatic or non-aromatic carbocyclic rings and two or more vinyl ether structures, per molecule,
   wherein the oxetane-containing vinyl ether compound is represented by the following Formula (1) (1a), (1b), (1c) or (1d):

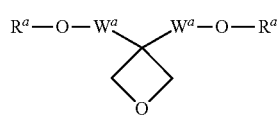

(1a)

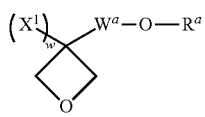

(1b)

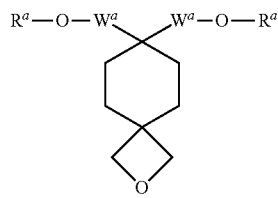

(1c)

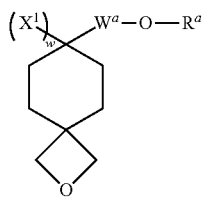

(1d)

wherein $R^a$ represents a substituted or unsubstituted vinyl group represented by following Formula (2):

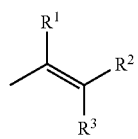

(2)

wherein each of $R^1$, $R^2$, and $R^3$ independently represents hydrogen atom or an alkyl group containing one to four carbon atoms;
$W^a$ is a linkage connecting between a substituted or unsubstituted vinyloxy group (—$OR^a$ group) and the oxetane ring or the cyclohexane ring that forms a spiro structure with the oxetane ring, and represents a single bond or an organic group having a valence in the number of (m+1);
$X^1$ is a substituent of oxetane ring;
"w" is 0 or 1, and
wherein at least one of $W^a$ and $X^1$ in Formula (1b) contains one or more aromatic or non-aromatic carbocyclic rings.

2. An alicyclic epoxy-containing vinyl ether compound represented by the following Formula (3a), (3c') or (3d):

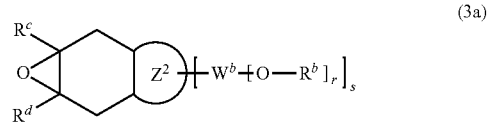

(3a)

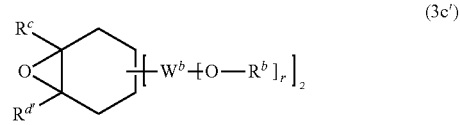

(3c')

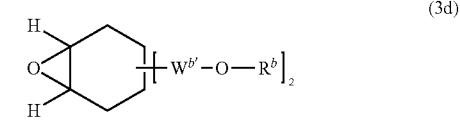

(3d)

wherein Ring $Z^2$ represents a non-aromatic carbocyclic ring;
wherein $R^b$ represents a substituted or unsubstituted vinyl group represented by the following Formula (4):

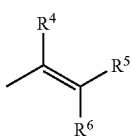

(4)

wherein each of $R^4$, $R^5$ and $R^6$ independently represents hydrogen atom or an alkyl group containing one to four carbon atoms;
$W^b$ is a linkage connecting between a substituted or unsubstituted vinyloxy group (—$OR^b$ group) and cyclohexane ring or Ring $Z^2$ and represents a single bond or an organic group having a valence in the number of (r+1);
$W^{b'}$ is a single bond; a bivalent hydrocarbon group containing one to six carbon atoms; or a bivalent organic group in which one or more hydrocarbon group containing one to six carbon atoms is connected with at least one selected from the group consisting of oxygen atom (—O—), sulfur atom (—S—), and amino group (—NH—);
each of $R^c$ and $R^d$ independently represents hydrogen atom or an alkyl group;
$R^{d'}$ is an alkyl group containing one to six carbon atoms;
"r" denotes 1 or 2; and
"s" denotes 1 or 2,
wherein, when any of "r" and "s" is 2, corresponding two parenthesized substituents may be the same as or different from each other.

3. A polymerizable composition comprising:
   (i) the oxetane-containing vinyl ether compound of claim 1 and/or the alicyclic epoxy-containing vinyl ether compound of claim 2; and
   (ii) a polymerization initiator.

4. A cured article as a polymerized product of a polymerizable composition comprising:
   (i) an oxetane-containing vinyl ether compound comprising:
      (a) at least one oxetane ring; and
      (b) one or more aromatic or non-aromatic carbocyclic rings, two or more vinyl ether structures, or
one or more aromatic or non-aromatic carbocyclic rings and two or more vinyl ether structures, per molecule,
wherein the oxetane-containing vinyl ether compound is represented by the following Formula (1) (1a), (1b), (1c) or (1d):

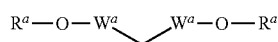
(1a)

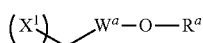
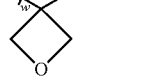
(1b)

(1c)

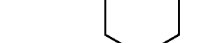

(1d)

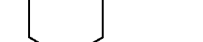

wherein $R^a$ represents a substituted or unsubstituted vinyl group represented by following Formula (2):

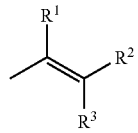
(2)

wherein each of $R^1$, $R^2$, and $R^3$ independently represents hydrogen atom or an alkyl group containing one to four carbon atoms;
$W^a$ is a linkage connecting between a substituted or unsubstituted vinyloxy group (—$OR^a$ group) and the oxetane ring or the cyclohexane ring that forms a Spiro structure with the oxetane ring, and represents a single bond or an organic group having a valence in the number of (m+1);
$X^1$ is a substituent of oxetane ring;
"w" is 0 or 1, and
wherein at least one of $W^a$ and $X^1$ in Formula (1b) contains one or more aromatic or non-aromatic carbocyclic rings, and/or an alicyclic epoxy-containing vinyl ether compound represented by the following Formula (3a), (3c') or (3d):

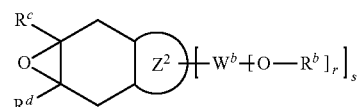
(3a)

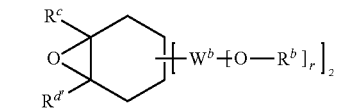
(3c')

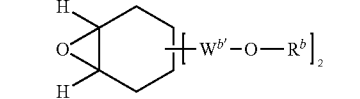
(3d)

wherein Ring $Z^2$ represents a non-aromatic carbocyclic ring;
wherein $R^b$ represents a substituted or unsubstituted vinyl group represented by the following Formula (4):

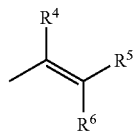
(4)

wherein each of $R^4$, $R^5$ and $R^6$ independently represents hydrogen atom or an alkyl group containing one to four carbon atoms;
$W^b$ is a linkage connecting between a substituted or unsubstituted vinyloxy group (—$OR^b$ group) and cyclohexane ring or Ring $Z^2$ and represents a single bond or an organic group having a valence in the number of (r+1);
$W^{b'}$ is a single bond; a bivalent hydrocarbon group containing one to six carbon atoms; or a bivalent organic group in which one or more hydrocarbon group containing one to six carbon atoms is connected with at least one selected from the group consisting of oxygen atom (—O—), sulfur atom (—S—), and amino group (—NH—);
each of $R^c$ and $R^d$ independently represents hydrogen atom or an alkyl group;
$R^{d'}$ is an alkyl group containing one to six carbon atoms;
"r" denotes 1 or 2; and
"s" denotes 1 or 2,
wherein, when any of "r" and "s" is 2, corresponding two parenthesized substituents may be the same as or different from each other; and
(ii) a polymerization initiator.

\* \* \* \* \*